(12) United States Patent
Xu et al.

(10) Patent No.: US 10,980,508 B2
(45) Date of Patent: Apr. 20, 2021

(54) SYSTEM AND METHOD FOR INTEGRATED BIOPSY AND THERAPY

(75) Inventors: Sheng Xu, Rockville, MD (US); Jochen Kruecker, Washington, DC (US); Bradford Johns Wood, Potomoc, MD (US)

(73) Assignees: KONINKLIJKE PHILIPS N.V., Eindhoven (NL); THE UNITED STATES OF AMERICA, DEPARTMENT OF HEALTH AND HUMAN SERVICES

( * ) Notice: Subject to any disclaimer, the term of this patent is extended or adjusted under 35 U.S.C. 154(b) by 877 days.

(21) Appl. No.: 13/321,836

(22) PCT Filed: May 14, 2010

(86) PCT No.: PCT/IB2010/052152
§ 371 (c)(1),
(2), (4) Date: Nov. 22, 2011

(87) PCT Pub. No.: WO2010/140075
PCT Pub. Date: Dec. 9, 2010

(65) Prior Publication Data
US 2012/0071749 A1  Mar. 22, 2012

Related U.S. Application Data

(60) Provisional application No. 61/184,322, filed on Jun. 5, 2009.

(51) Int. Cl.
*A61B 8/08*    (2006.01)
*A61B 8/12*    (2006.01)
(Continued)

(52) U.S. Cl.
CPC .......... *A61B 8/0833* (2013.01); *A61B 6/5247* (2013.01); *A61B 8/0841* (2013.01);
(Continued)

(58) Field of Classification Search
CPC ...... A61B 2034/107; A61B 2017/3413; A61B 34/20
(Continued)

(56) References Cited

U.S. PATENT DOCUMENTS 6,505,063 B2   1/2003  Van Den Brink et al.
6,675,037 B1   1/2004  Tsekos
(Continued)

FOREIGN PATENT DOCUMENTS

CN    101322652 A    12/2008
WO    WO199858588    12/1998
(Continued)

OTHER PUBLICATIONS

"Prostatic Transrectal Ultrasound (TRUS) Guided Biopsy Schemes and TRUS Prostatic Lesion-Guided Biopsies" by V. Scattoni et al. European Urology Supplements. 1, pp. 28-34, 2002 (Year: 2002).*
(Continued)

*Primary Examiner* — Jason M Ip
(74) *Attorney, Agent, or Firm* — Sherry Womack Austin

(57) ABSTRACT

A system and method for integrating diagnosis and treatment for internal tissues includes imaging (202) at least a portion of an internal organ of a subject using a first technology capable of differentiating tissue types, and targeting (205) and accessing biopsy sites using images of the first technology fused with images of a second technology capable of real-time image updates. Treatment of a biopsy site is planned (207) using the images of the first technology. Instruments for treating the biopsy site are guided (210) by fusing (208) the images of the first technology with the images of the second technology.

25 Claims, 6 Drawing Sheets

(51) Int. Cl.
*A61B 34/20* (2016.01)
*A61B 6/00* (2006.01)
*A61B 10/02* (2006.01)
A61B 6/12 (2006.01)
A61B 18/02 (2006.01)
A61B 18/14 (2006.01)
A61B 90/00 (2016.01)

(52) U.S. Cl.
CPC .............. *A61B 8/12* (2013.01); *A61B 8/5238* (2013.01); *A61B 10/0233* (2013.01); *A61B 6/12* (2013.01); *A61B 18/02* (2013.01); *A61B 18/14* (2013.01); *A61B 34/20* (2016.02); *A61B 2090/374* (2016.02); *A61B 2090/378* (2016.02)

(58) Field of Classification Search
USPC .................. 600/407, 410, 411, 415, 437
See application file for complete search history.

(56) References Cited

U.S. PATENT DOCUMENTS

| | | | |
|---|---|---|---|
| 8,447,384 B2 | 5/2013 | Xu et al. | |
| 8,731,264 B2 | 5/2014 | Kruecker et al. | |
| 8,885,897 B2 | 11/2014 | Xu | |
| 9,504,453 B2 | 11/2016 | Haberstich et al. | |
| 2007/0230757 A1 | 10/2007 | Trachtenberg et al. | |
| 2008/0091106 A1 | 4/2008 | Kim et al. | |
| 2008/0119725 A1 | 5/2008 | Miranda et al. | |
| 2008/0132782 A1 | 6/2008 | Rueckmann et al. | |
| 2008/0161687 A1* | 7/2008 | Suri | A61B 8/0833 600/437 |
| 2008/0234569 A1 | 9/2008 | Tidhar et al. | |
| 2009/0093715 A1* | 4/2009 | Downey | A61B 8/0833 600/437 |
| 2010/0249595 A1 | 9/2010 | Xu et al. | |

FOREIGN PATENT DOCUMENTS

| | | |
|---|---|---|
| WO | WO2006060613 | 6/2006 |
| WO | WO2006089426 | 8/2006 |
| WO | WO2008065600 | 6/2008 |

OTHER PUBLICATIONS

D'Amico et al., "Transperineal Magnetic Resonance Image Guided Prostate Biopsy", the Journal of Urology, vol. 164, Aug. 2000, pp. 385-387.

Ocak et al., "Dynamic Contrast-Enhanced MRI of Prostate Cancer at 3 T: A Study of Pharmacokinetic Parameters", AJR:189, Oct. 2007, pp. W192-W201.

Xu, S. et al. "Real-time MRI-TRUS fusion for guidance of targeted prostate biopsies", Journal of Computer Aided Surgery, vol. 13, Issue 5 Sep. 2008 , pp. 255-264.

\* cited by examiner

SYSTEM AND METHOD FOR INTEGRATED BIOPSY AND THERAPY

This invention was made in the performance of a Cooperative Research and Development Agreement with the United States Public Health Service (CRADA No. NCI-NIHCC-01864). The Government of the United States has certain rights in the invention.

This disclosure relates to imaging technology, and more particularly to systems and methods that integrate biopsy imaging with therapeutic procedures.

Prostate cancer affects one in every six men in the western world at some point in their lives. Because of the lack of imaging and image guidance, conventional (blind) sextant biopsy used for diagnosis is painful and unreliable. As a result, prostate cancer is over-diagnosed and over-treated. In therapy, almost all prostate cancers are currently treated by surgery or whole-prostate radiation therapy, leading to significant side effects.

Today, prostate cancer care is performed without ample visual feedback. A biopsy is ultrasound guided because ultrasound is real-time and cost-effective and can be employed to visualize the prostate. Unfortunately, ultrasound does not show a cancer. So, instead of going for the cancer in a targeted, image-guided way, the biopsy is blindly sampled with a sextant biopsy, which results in an up to a 30% false negative rate. One problem with image guidance also extends to prostate cancer therapy. Without adequate guidance, therapy approaches remain limited to whole-gland therapy, which shows significant side effects such as urinary incontinence and impotence in a large number of patients. Therefore, a move away from blind and whole-gland approaches needs to be made.

In accordance with the present principles, a move toward targeted, localized procedures is made. Magnetic resonance imaging (MRI) is currently the most promising imaging modality for depicting prostate cancer and other abnormalities and cancers on internal organs. Magnetic resonance imaging (MRI) guidance is not compatible with current workflows, however. Since MRI is expensive and typically not used for procedure guidance, it is desirable to fuse pre-operative MRI with real-time transrectal ultrasound (TRUS) during an intervention related to the prostate. As a result, the MRI information can be used during the intervention outside the MRI suite. In a previous work, the present inventors developed an image fusion system for MRI/TRUS guided targeted biopsy. The fusion system utilized electromagnetic (EM) tracking for spatial localization of an ultrasound probe. Spatial tracking of the probe is enabled by attaching a biopsy guide to the probe that is customized with electromagnetic tracking sensors.

Although MRI has good sensitivity and specificity in prostate cancer diagnosis, it may not be sufficiently definitive. MRI may miss identifying prostate lesions, suggesting that MRI-targeted prostate biopsy alone may be insufficient. In accordance with the present embodiments, a sextant biopsy employs a targeted biopsy to increase the yield of the sextant biopsy and detect lesions that are not recognizable by MRI.

In the current standard care of prostate cancer, prostate biopsy and therapy are two separate procedures. Therefore, even if lesions are found in the sextant biopsy procedure, it is difficult to go back exactly to the same location during the therapy to treat the lesion. The position information of sextant biopsy is under-utilized. With the tracked biopsy and image fusion, the gap between prostate biopsy and focal therapy can be bridged by using the same diagnosis MRI image to document biopsy, plan for therapy and provide image guidance.

An integrated prostate cancer suite in accordance with the present principles enables physicians to seamlessly plan, navigate, execute and monitor a biopsy or focal therapy procedure. It is based on the fusion of pre-acquired MRI with live transrectal ultrasound (TRUS): target information from MRI augments TRUS guidance, which improves the accuracy of biopsy and focal treatment.

A system and method combine biopsy and therapy by using a same diagnostic MRI image to document biopsy, plan for therapy and provide image guidance. In one embodiment, the system/method includes the following: (1) performing tracked sextant with MRI-targeted biopsies for prostate cancer detection, (2) identifying all the biopsy sites on MRI using MRI/TRUS fusion, (3) planning focal therapy on the MRI image using the pathology results of the biopsy specimens, and (4) fusing the MRI-based treatment plan with real-time TRUS for focal therapy guidance. Combining sextant biopsy with targeted biopsy increases the yield of sextant biopsy and detects lesions that are not recognizable by MRI. Prostate biopsy and therapy can be carried out at different times, but the biopsy findings are used to guide the therapy. The system and method are adaptable and not limited to treatment of prostate cancer.

A system and method for integrating diagnosis and treatment for internal tissues includes imaging at least a portion of an internal organ of a subject using a first technology capable of differentiating tissue types, and targeting and accessing biopsy sites using images of the first technology fused with images of a second technology capable of real-time image updates. Treatment of a biopsy site is planned using the images of the first technology. Target information that may be used for treatment planning includes positive biopsy locations and/or suspicious regions of diagnostic images (e.g. MRI or MRI+PET fusion). Instruments for treating the biopsy site are guided by fusing the images of the first technology with the images of the second technology.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
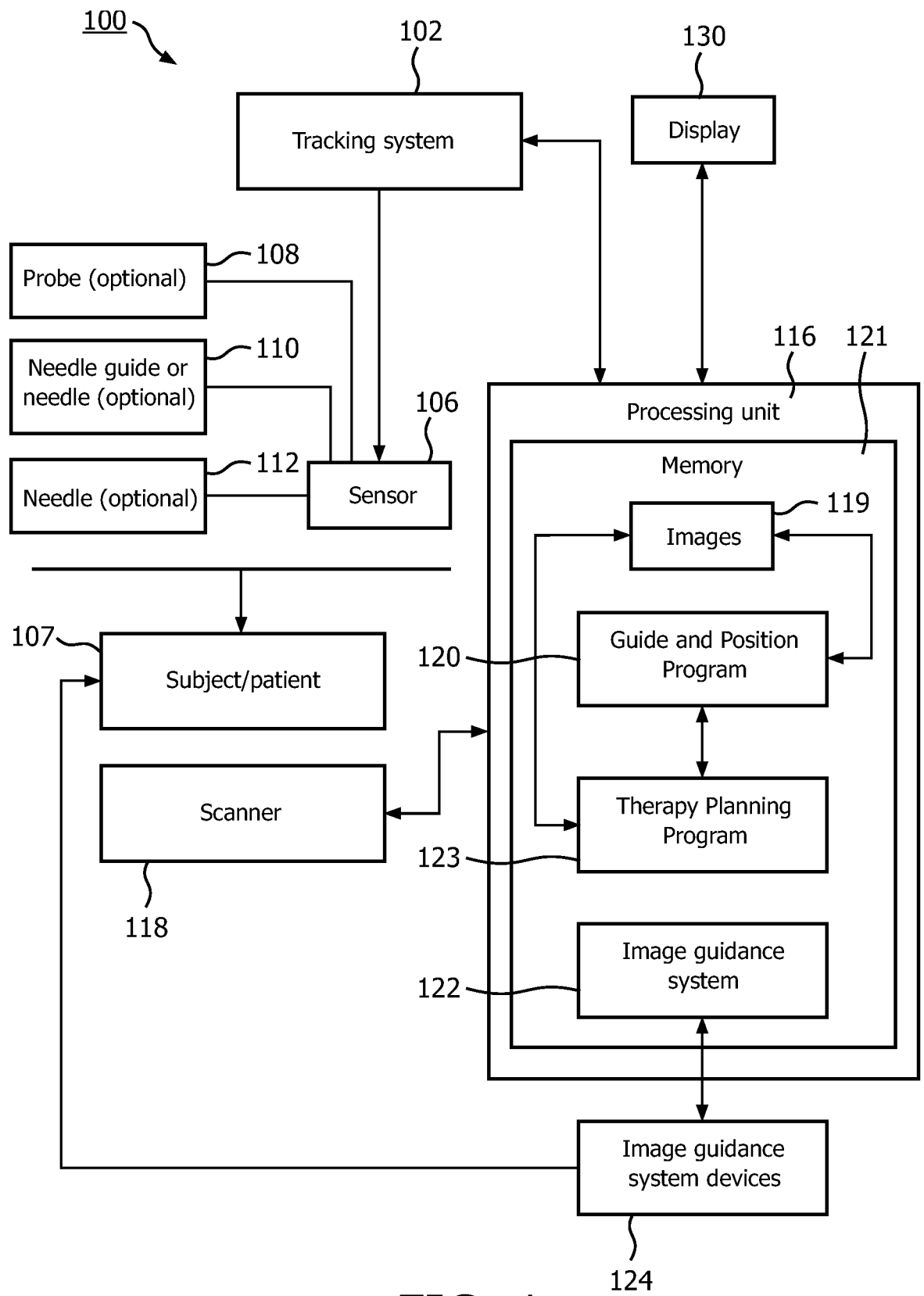
FIG. 1 is a block diagram showing a system and method for integrating diagnosis and treatment for internal tissues in accordance with the present principles.

The present disclosure describes systems and methods for fusing imaging technologies and employing biopsy information in therapy or subsequent procedures. The present embodiments will be illustratively described in terms of prostate cancer diagnosis and therapy. It should be understood that the present principles may be employed for other cancers or procedures and should not be construed as limited by the illustrative examples. In one particularly useful application, MRI imaging and MRI/ultrasound fusion technologies are employed to enable lesion targeted biopsy and focal therapy which may reduce side effects. (E.g., conventional prostate cancer biopsy and therapy are blind, whole-gland procedures with significant side effects).

MRI is insufficient to detect all prostate cancer. To improve the outcome of the procedures, a method in accordance with one embodiment includes performing a tracked sextant with MRI-targeted biopsies for prostate cancer detection; identifying all the biopsy sites on the MRI using MRI/TRUS fusion; planning focal therapy on the MRI image using the pathology results of the biopsy specimens and fusing the MRI-based treatment plan with real-time TRUS for focal therapy guidance. This method bridges the gap between prostate biopsy and therapy, increases the yield of biopsy and reduces the side effects of therapy.

It should be understood that the present disclosure is applicable for any cancer or disease in any organism. The elements depicted in the FIGS. may be implemented in various combinations of hardware and/or software and provide functions which may be combined in a single element or multiple elements.

Furthermore, the present principles can take the form of a computer program product accessible from a computer-usable or computer-readable medium providing program code for use by or in connection with a computer or any instruction execution system. A computer-usable or computer readable medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code may include at least one processor coupled directly or indirectly to memory elements through a system bus. The processor or processing system may be provided with the scope system or provided independently of the scope system. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Referring now to the drawings in which like numerals represent the same or similar elements and initially to FIG. 1, a system 100 is depicted for combining biopsy information with therapy. System 100 includes a tracking system 102 employed during an ultrasound-guided medical procedure. The tracking system 102 may include, e.g., an electromagnetic tracking system with a field generator placed near a patient or subject 107 to provide positional coordinates of a tracking sensor(s) 106 during a procedure. In one embodiment, the tracking sensor 106 is attached to an ultrasound probe 108. Alternatively, a needle guide 110 may be provided with tracking sensors 106 which can be attached to the ultrasound probe 108. Optionally, the tracking sensor 106 may be attached to a biopsy needle 112. The equipment and methodology may be varied in accordance with the procedure and anatomy being analyzed and treated.

A processing unit 116 is connected to the tracking system 102 and an ultrasound scanner 118 (or other real-time scanning technology). The processing unit 116 simultaneously obtains ultrasound images from the scanner 118, and corresponding position information from the sensor 106. The processing unit 116 can be a workstation, or may be part of the ultrasound scanner 118. The processing unit 116 includes memory 121 which includes a software program 120 for execution on the processing unit 116 that guides an MRI-targeted biopsy, acquires and stores real-time ultrasound images, together with the volume's tracking system coordinates provided by the sensor 106, identifies the needle 110 or other interventional device in real-time or recorded ultrasound, and transforms the biopsy sample's position to a corresponding spot in an MRI image 119. Processing unit 116 includes software 123 for focal therapy planning based on the MRI image 119, the biopsy positions in the MRI image 119 and pathology results of the biopsies.

An image guidance system 122 executes on processing unit 116 for focal therapy that permits fusing a treatment plan with real-time ultrasonic imaging, and guiding targeted focal therapy based on the plan. Optionally, the image guidance system 122 of the biopsy can be adapted for focal therapy, or the image guidance system 122 for focal therapy can be based on mechanical devices 124 with position encoders and template grids. Such mechanical devices can therefore be accurately tracked with reference to image positions obtained in real-time and fused with other images (e.g., MRI).

Advantageously, the MRI images and the scanner images (e.g., ultrasonic images) are combined or fused using device tracking (e.g., the ultrasound probe, a registration pointer etc.) and/or image registration. Once registered, real-time images (e.g., ultrasound images) may benefit from the detailed MRI images (or other type images) since the fused images provide a complete set of information. The information is advantageously employed for both diagnosis and for treatment, and the fused image can be updated in real-time to track diagnosis, analysis and treatment. Scanned and fused images may be viewed using one or more display devices 130, which provide visual feedback for users to interface with the system 100.

Figure 2:
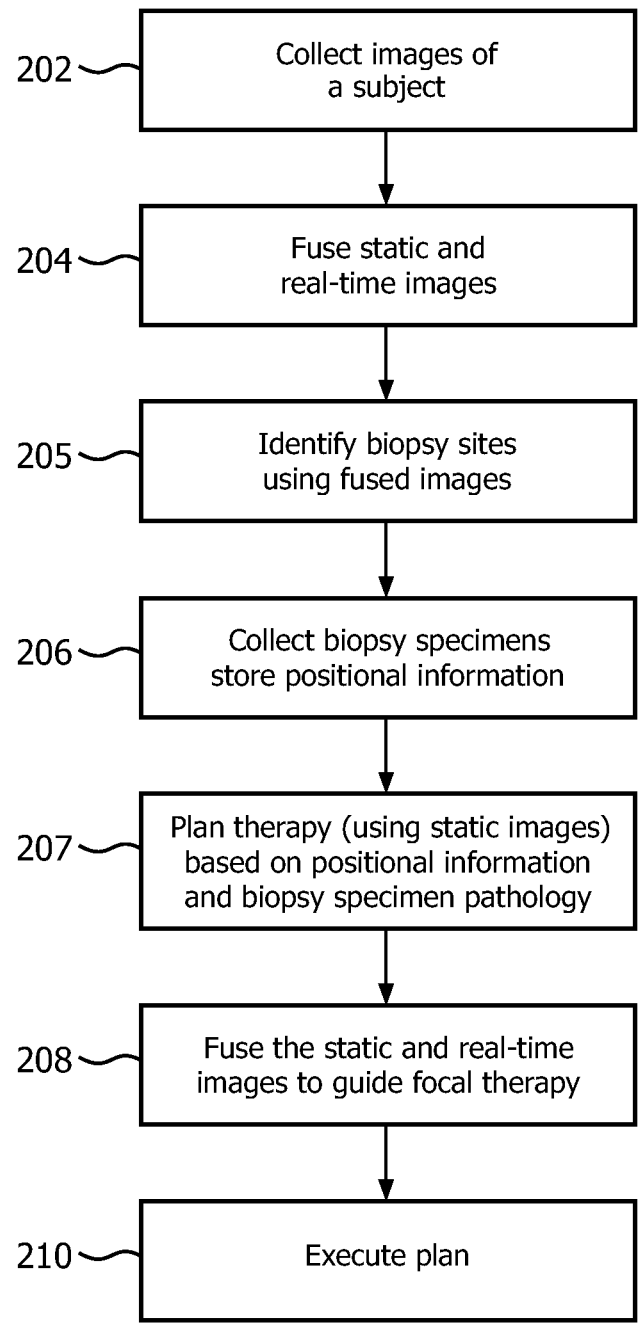
FIG. 2 is a block/flow diagram showing a system/method for integrating diagnosis and treatment for internal tissues in accordance with the present principles.

Referring to FIG. 2, a block/flow diagram illustratively depicts a system/method for diagnosis (e.g., biopsy) and treatment (e.g., focal therapy) for a surgical procedure. In the present example for prostate cancer, the system/method combines a tracked sextant and MRI-targeted biopsies for prostate cancer detection. In block 202, images are collected for a subject. The images preferably employ a technology capable of differentiating between tissues (e.g., MRI technology). In block 204, static (e.g., MRI or other technology) images are fused with real-time updated images (e.g., ultrasonic images) by performing a registration method or by employing tracked coordinate systems. In block 205, all the biopsy sites are identified on the MRI using MRI/TRUS fusion. The biopsy site(s) is targeted and samples are obtained using guided interventional instruments in block

206. Positional information for the biopsy site(s) is recorded and stored for use later in therapy/treatment.

The MRI image is then used to plan for focal therapy based on a pathology examination of the biopsy specimens in block 207. The plan (static image) is fused with real-time images (e.g., TRUS) to guide focal therapy in block 208. The plan is carried out or executed using the MRI and TRUS information in the fused image in block 210.

MRI-targeted biopsy: The prostate MR image is acquired first and transferred to a workstation (e.g., 116, FIG. 1). The patient is then positioned on an examination table and a 2D TRUS probe with tracking sensors is inserted into the rectum. At the beginning of the TRUS procedure, the operator performs a 2D axial sweep (prostate base to apex) such that the series of 2D ultrasound images covers the entire volume of the prostate. (In an alternative, a 3D ultrasound probe can be used to obtain the prostate volume.) The images and corresponding tracking data from the tracking sensors are transferred to the workstation in real-time. Based on these images and tracking data, a volumetric ultrasound image is immediately reconstructed on the workstation. The MR image and ultrasound volume are then spatially aligned. During the procedure, the operator manually holds the 2D probe to scan the prostate. Spatial tracking of the ultrasound probe, and registering MRI coordinate system with the tracking coordinate system, enables real-time fusion of the live ultrasound image with the spatially corresponding multi-planar reconstruction (MPR) from the MRI scan.

When prostate motion results in misalignment between the ultrasound and MR images, image-based registration between the real-time 2D ultrasound images and the static ultrasound volume will be carried out to recover the correct MRI/TRUS fusion. A tissue sample may be obtained when the needle is aligned with the target.

Tracked sextant biopsy: Tracked sextant biopsy can be carried out with a targeted biopsy under the same clinical setup. The order between them is not important. The physician can ignore the MRI image and perform sextant biopsy under TRUS guidance only. The TRUS images and the corresponding tracking information of the probe can be recorded. The locations of sextant biopsy can be (retrospectively) identified on the MRI using MRI/TRUS fusion as shown in FIGS. 3A-3D.

Figure 3A:
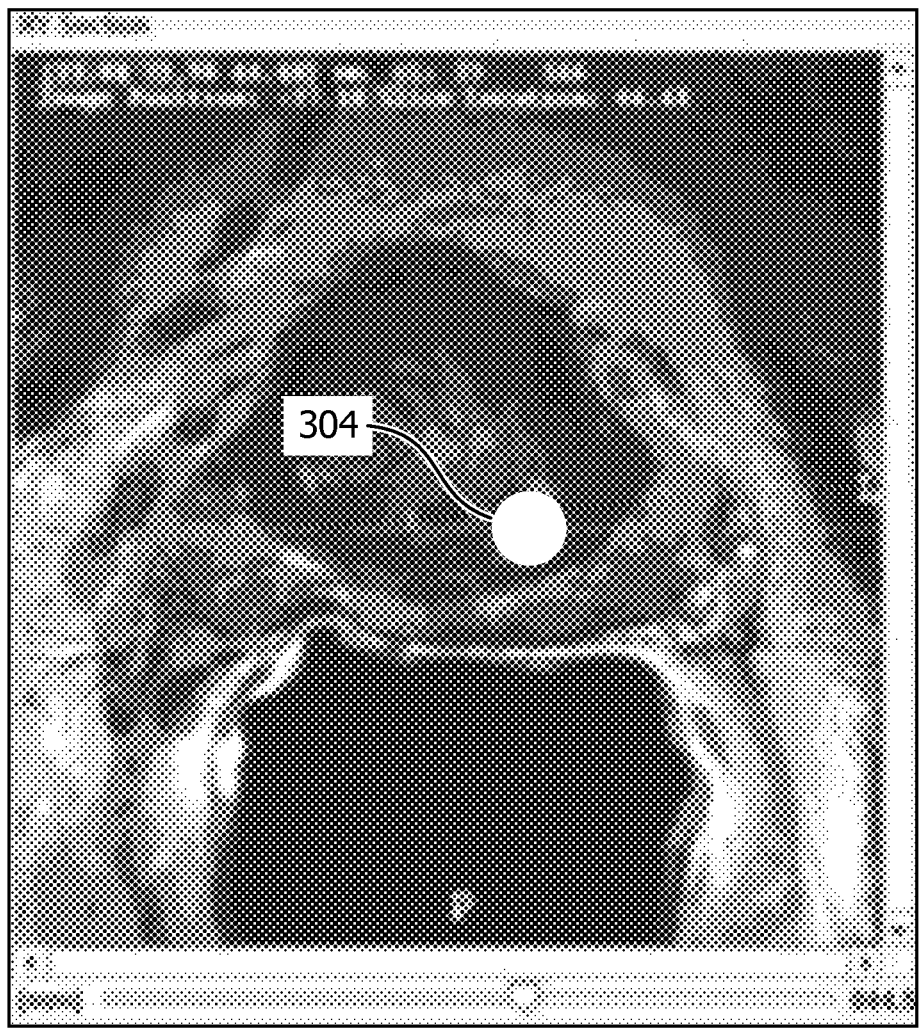
FIGS. 3A-3C are MRI images showing three views of a specimen employed in accordance with an illustrative procedure.
Figure 3B:
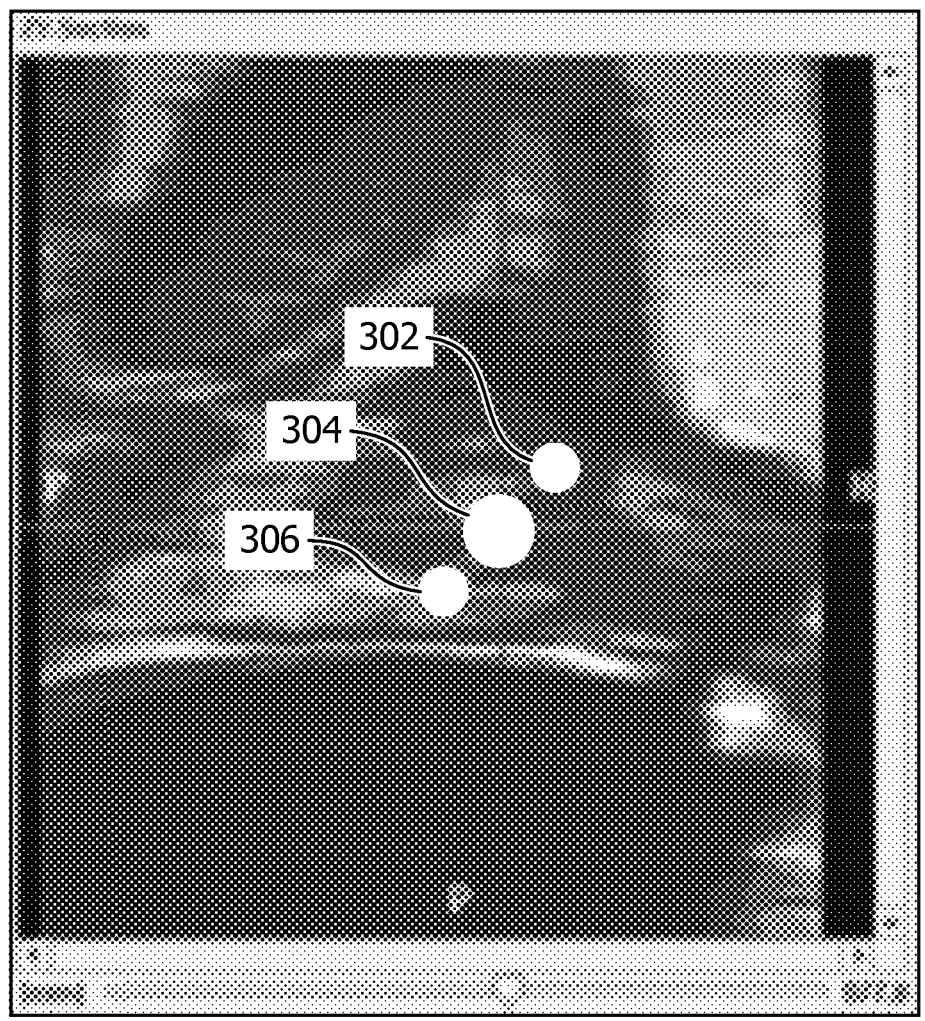
Figure 3C:
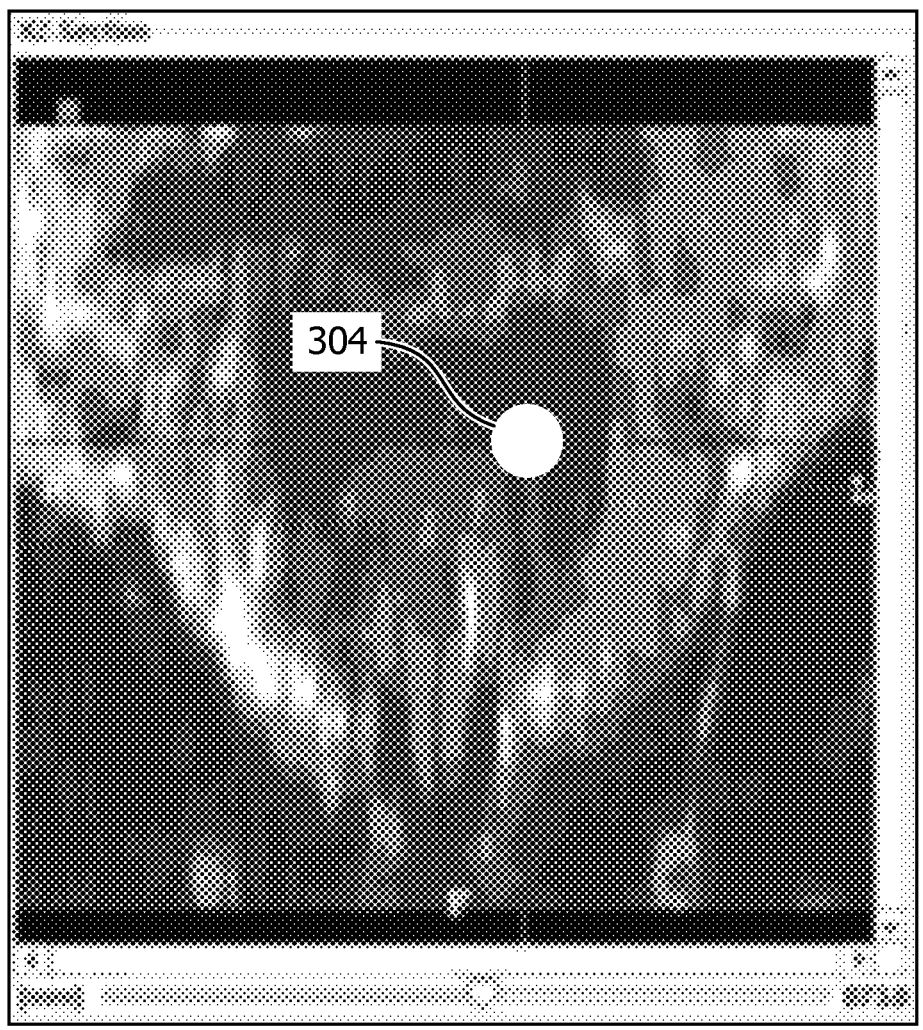
Figure 3D:
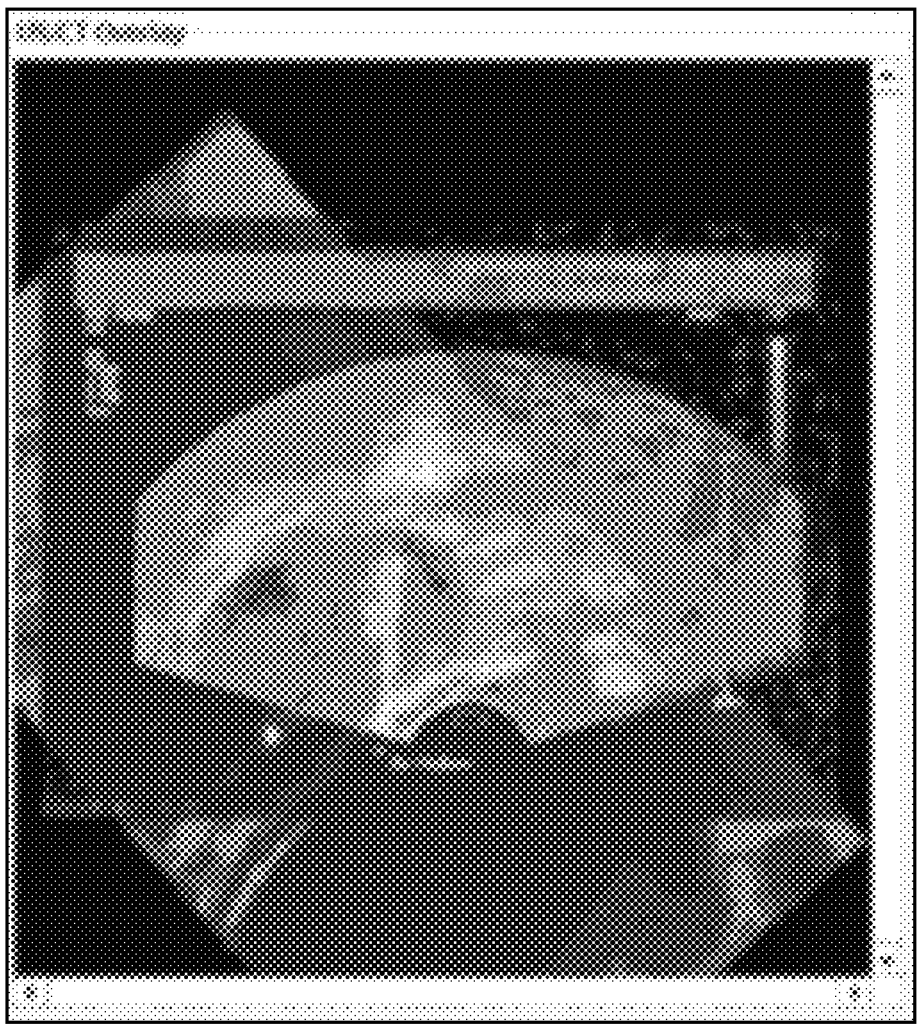
FIG. 3D is a fused image combining an MRI with and ultrasound image in accordance with an illustrative embodiment.

Referring to FIGS. 3A-3D, images of a prostate region in a subject are illustratively depicted. FIGS. 3A-3D show the development of an MRI/TRUS fusion for a biopsy needle firing. FIG. 3D shows an alpha-blending of MRI and TRUS images. This fusion provides the accuracy needed for identifying particular tissues along with the dynamic and real-time images provided by ultrasound. FIGS. 3A-3C show axial, sagittal and coronal views, respectively, of an MRI focused on a mid-point of a specimen to be analyzed and treated in a patient. Markers 302, 304 and 306 show two end points (302 and 306) and a mid-point (304) of the biopsy specimen. The markers 302, 304 and 306 indicate a biopsy needle trajectory.

While MRI images are described, instead of using an MRI volume for diagnosis, procedure guidance and treatment planning, other 3D (or 4D) image volumes may be employed (e.g., computed tomography (CT), positron emission tomography (PET), single photon emission computer tomography (SPECT), 3D ultrasound, and cancer probability mapping, and image fusion of multiple diagnostic images such as MRI, PET and contrast ultrasound, etc.). Further, instead of using electromagnetic tracking, optical, mechanical or other tracking systems may be employed.

After the locations of sextant and targeted biopsies are identified on the MRI images, the locations can be correlated with the pathology examination of the specimens collected during the biopsy. A treatment plan can be made on the MRI image to cover all the cancer locations and spare the healthy tissue. Both positive and negative biopsy cores can be used to plan focal therapy. In other embodiments, instead of performing separate sextant and MRI-targeted biopsies, the sites of the sextant biopsy can be optimized based on the MRI target locations to maximize the probability for finding cancer. The processes described may be applied to ultrasound/MR images of the breast, liver, kidney or other soft-tissue targets.

The workflow of focal therapy is similar to that of the MRI-targeted biopsy. Instead of using the MRI targets, the treatment plan can be highlighted on real-time TRUS for procedure guidance. The therapy modality can be any modality suitable for focal therapy, such as cryo-ablation, radiofrequency ablation or other ablative therapies, brachytherapy or other radiation-based therapy, or photodynamic therapy.

Advantageously, results from several biopsies—even obtained on different times/dates—can be combined by registering a reconstructed ultrasound volume obtained for each biopsy with the same baseline MRI scan, or by registering the ultrasound sweeps with different MRI scans which in turn are spatially co-registered. The treatment delivery locations can be tracked and recorded as well with the same tracking system used to track biopsy locations. The system can then also be used for optimizing multiple, sequential treatments over time, by considering prior treated regions in the treatment plan for subsequent/repeat treatments (e.g., avoiding unnecessary duplication of treatment in the same area). In one embodiment, electronic images may be colorized or otherwise marked to identify treated regions or regions yet to be treated or both. Other manipulations of images data are also contemplated.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods (which are intended to be illustrative and not limiting), it is noted that modifications and variations can be made by persons skilled in the art in light of the above teachings. It is therefore to be understood that changes may be made in the particular embodiments of the disclosure disclosed which are within the scope and spirit of the embodiments disclosed herein as outlined by the appended claims. Having thus described the details and particularity required by the patent laws, what is claimed and desired protected by Letters Patent is set forth in the appended claims.

The invention claimed is:

1. A method for integrating diagnosis and treatment for internal tissues, comprising acts of:

imaging at least a portion of an internal organ of a subject using a first technology capable of differentiating tissue types to obtain static images;

simultaneously obtaining real-time images from a tracked probe of a second technology and obtaining probe position information corresponding to positions of the tracked probe, the tracked probe having a sensor configured to provide the probe position information, the second technology being of configured to perform real-time image updates and being different from the first technology;

forming a first fused image which includes a static image of the static images of the first technology combined with a real-time image of the real-time images of the second technology based on the probe position information;

identifying biopsy sites on at least one static image of the static images of the first technology using the first fused image;

targeting and accessing the identified biopsy sites;

obtaining site positional information of the targeted and accessed biopsy sites from the sensor of the tracked probe located at the targeted and accessed biopsy sites;

transforming the site positional information of the targeted and accessed biopsy sites to corresponding position information in the static images to form transformed static images;

planning treatment of at least one of the biopsy sites to form a plan static image from the static images based on the transformed static images including the site positional information of the targeted and accessed biopsy sites that were identified using the first fused image and based on pathology results of biopsy specimens obtained at the targeted and accessed biopsy sites;

forming a second fused image which includes the plan static image combined with the real-time image;

guiding an instrument for treating the at least one biopsy site using the second fused image;

constructing a volumetric ultrasound image based on the real-time images and the probe position information;

spatially aligning the static images and the real-time images to form at least the first fused image; and registering the real-time image with the volumetric ultrasound image to recover the first fused image in response to misalignment between the real-time images and the volumetric ultrasound image.

2. The method as recited in claim 1, wherein the first technology includes magnetic resonance imaging (MRI) and the second technology includes ultrasonic imaging.

3. The method as recited in claim 2, wherein the internal organ includes a prostate and the act of targeting and accessing the identified biopsy sites using the first fused image includes performing a sextant and magnetic resonance tracked biopsy.

4. The method as recited in claim 1, wherein the internal organ includes any soft-tissue organ.

5. The method as recited in claim 1, wherein the act of targeting and accessing the identified biopsy sites includes tracking the tracked probe in the first fused image using a tracking system.

6. The method as recited in claim 1, wherein the act of guiding the instrument for treating the at least one biopsy site includes guiding focal therapy using the second fused image.

7. The method as recited in claim 6, wherein the focal therapy includes at least one of an ablative therapy, a radiation-based therapy, and a photodynamic therapy.

8. The method as recited in claim 6, wherein the act of guiding the instrument for treating the at least one biopsy site includes adapting an image guidance system employed for biopsy to perform the focal therapy.

9. The method as recited in claim 6, wherein the act of guiding the instrument for treating the at least one biopsy site includes employing a mechanical device for the focal therapy by using one of a position encoder and a template grid.

10. A method for integrating diagnosis and treatment for internal tissues, comprising acts of:

imaging at least a portion of an internal organ of a subject using magnetic resonance imaging (MRI) to obtain MRI images;

simultaneously obtaining from a tracked probe ultrasound images and probe position information corresponding to positions of the tracked probe;

forming a first fused image which includes an MRI image of the MRI images combined with an ultrasound image of the ultrasound images based on the probe position information;

updating in real-time the first fused image in response to misalignment between the MRI image and the ultrasound image;

identifying biopsy sites on the MRI images using the first fused image;

targeting and accessing the identified biopsy sites;

obtaining site positional information of the targeted and accessed biopsy sites from the tracked probe located at the targeted and accessed biopsy sites;

transforming the site positional information of the targeted and accessed biopsy sites to corresponding position information in the MRI images to form transformed MRI images;

planning treatment of at least one of the biopsy sites to form a plan MRI image from the MRI images based on the transformed MRI images including the site positional information of the targeted and accessed biopsy sites that were identified using the first fused image and based on pathology results of biopsy specimens obtained at the targeted and accessed biopsy sites;

forming a second fused image which includes the plan MRI image combined with the ultrasound image; and guiding an instrument for treating the at least one biopsy site using the second fused image.

11. The method as recited in claim 10, wherein the internal organ includes a prostate and the act of targeting and accessing the identified biopsy sites includes performing at least one of a sextant, a blind, and a magnetic resonance tracked biopsy.

12. The method as recited in claim 10, wherein the act of targeting and accessing the identified biopsy sites includes tracking the tracked probe in the first fused image using a tracking system.

13. The method as recited in claim 10, wherein the act of guiding the instrument for treating the at least one biopsy site includes guiding focal therapy using the second fused image.

14. The method as recited in claim 13, wherein the focal therapy includes at least one of an ablative therapy, a radiation-based therapy, and a photodynamic therapy.

15. The method as recited in claim 13, wherein the act of guiding the instruments for treating the at least one biopsy site includes adapting an image guidance system employed for biopsy to perform the focal therapy.

16. The method as recited in claim 13, wherein the act of guiding the instrument for treating the at least one biopsy site includes employing a mechanical device for the focal therapy by using one of a position encoder and a template grid.

17. A system for integrating diagnosis and treatment for internal tissues, comprising:
   a scanner configured to image at least a portion of an internal organ of a subject;
   a tracking system configured to track an interventional instrument for targeting and accessing biopsy sites in accordance with real-time images from the scanner, to obtain instrument position information corresponding to positions of the tracked interventional instrument, and to locate focal therapy sites corresponding therewith;
   a processor having associated memory storage for storing a program, the program configuring the processor to cause:
   based on the instrument position information, generation of first fused images which include static images taken with a first technology capable of differentiating tissue types combined with the real-time images taken in real-time by the scanner of a second technology which is different from the first technology,
   identification of the biopsy sites on at least one static image of the static images using the first fused images;
   target and access the identified biopsy sites;
   obtain site positional information of the targeted and accessed biopsy sites from the tracked interventional instrument located at the targeted and accessed biopsy sites;
   transform the site positional information of the targeted and accessed biopsy sites to corresponding position information in the static images to form transformed static images;
   plan treatment of at least one of the biopsy sites to form a plan static image from the static images based on the transformed static images including the site positional information of the targeted and accessed biopsy sites that were identified using the first fused image and based on pathology results of biopsy specimens obtained at the targeted and accessed biopsy sites;
   form a second fused image which includes the plan static image combined with the real-time image;
   guide a treatment instrument for treating the at least one biopsy site using the second fused image;
   construction of a volumetric ultrasound image based on the real-time images and the probe position information;
   spatial alignment of the static images and the real-time images to form at least the first fused image; and
   registration of the real-time image with the volumetric ultrasound image to recover the first fused image in response to misalignment between the real-time images and the volumetric ultrasound image.

18. The system as recited in claim 17, wherein the scanner includes an ultrasonic imaging scanner and the technology configured to differentiate tissue types includes magnetic resonance imaging (MRI).

19. The system as recited in claim 18, wherein the internal organ includes a prostate and the interventional instrument includes at least one of a sextant and a tracked biopsy device.

20. The system as recited in claim 17, wherein the internal organ includes any soft-tissue organ.

21. The system as recited in claim 17, wherein positions of the site positional information are employed for guiding focal therapy based on the pathology results.

22. The system as recited in claim 21, wherein the focal therapy includes at least one of an ablative therapy, a radiation-based therapy, and a photodynamic therapy.

23. The system as recited in claim 21, wherein the focal therapy employs mechanical instruments guided by using one of a position encoder and a template grid.

24. The system as recited in claim 17, wherein the site positional information includes at least one of positive biopsy location and suspicious region of diagnostic images.

25. The system as recited in claim 24, wherein the at least one positive biopsy location and suspicious region is found in a magnetic resonance imaging (MRI) image or a fused MRI and positron emission tomography (PET) image.

* * * * *